United States Patent

Satoh et al.

[11] Patent Number: 5,910,499
[45] Date of Patent: Jun. 8, 1999

[54] ANTIALLERGIC AGENT HAVING AN ANTI-OXIDANT ACTION

[75] Inventors: Toshio Satoh, Tokushima; Tetsuo Ebata, Kunitachi; Yasuo Kosaka, Matsudo, all of Japan

[73] Assignees: LTT Institute Co., Ltd.; Kuree Co., Ltd., both of Tokyo, Japan

[21] Appl. No.: 09/040,494

[22] Filed: Mar. 18, 1998

[30] Foreign Application Priority Data

Mar. 21, 1997 [JP] Japan .................................. 9-085558

[51] Int. Cl.$^6$ .................. A61K 31/495; C07D 295/088
[52] U.S. Cl. ........................................ 514/255; 544/396
[58] Field of Search ............................ 544/396; 514/255

[56] References Cited

U.S. PATENT DOCUMENTS 2,899,436  8/1959  Morren ...................................... 544/396
4,918,073  4/1990  Rüger et al. ............................... 544/396

FOREIGN PATENT DOCUMENTS 1212015  3/1960  France .

OTHER PUBLICATIONS

"Oxatomide: antiallergic/antispasmodic," Heinrich Koch, *Pharmacy International*, Mar. 1981, p. 50.

"Oxatomide, a new orally active drug which inhibits both the release and the effects of allergic mediators," F. Awouters et al., *Janssen Pharmaceutica*, May 16, 1977, pp. 1657–1659.

*Primary Examiner*—Emily Bernhardt
*Attorney, Agent, or Firm*—Price, Heneveld, Cooper, DeWitt & Litton

[57] ABSTRACT

An antiallergic agent having leucotriene production inhibiting action and antihistaminic action, which can be orally administered is provided; the antiallergic agent comprises a hydroquinone derivative of general formula

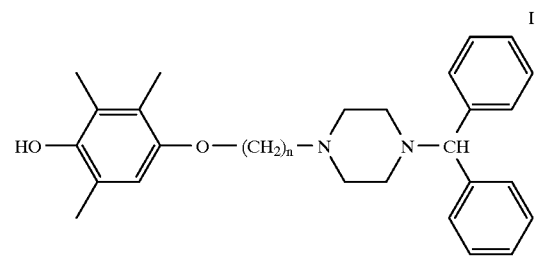

(wherein n represents an integer of 2–10).

23 Claims, 2 Drawing Sheets

EFFECT OF COMPOUND I AND THAT OF TRANILAST ON 48 HOURS HOMOLOGOUS PCA REACTION ON A RAT'S BACK SKIN

ANTIALLERGIC AGENT HAVING AN ANTI-OXIDANT ACTION

BACKGROUND OF THE INVENTION

1. Field of the Invention

The present invention relates to an antiallergic agent having an anti-oxidant action which comprises a hydroquinone derivatives.

2. Description of the Related Art

Presently, allergic diseases have been rapidly increasing and particularly in urban areas, three out of 10 people are suffering from allergic diseases such as asthma bronchiale, atopic dermatitis, pollenosis, and allergic rhinitis, and the treatment thereof is a national problem. Causes for this rapid increase include air pollution, food additives and many other problems, however, the background has not yet been made clear, and some of the problems are difficult to solve. Most fundamental prevention of allergy is to avoid the allergen, but even the identified allergens (for example *Cryptomeria japonica*) cannot be easily evaded in practice, and there are many cases in which the allergen is not identified, or allergens of many kinds are involved. Recently, for the asthma bronchiale, due to the development of a long acting bronchodilator, particularly an inhalant steroid, methods of controlling the attack has been progressed in order to reduce the symptoms, but it is far from the ultimate treatment.

Various antiallergic drugs have been developed for the purposes of preventive treatment, but the availability in the body, reflecting the complicated conditions of the allergic diseases, is far from the desirable level. Recently, leucotriene $C_4$, $D_4$ and $E_4$ receptor antagonists (ONO-1078) have come on the market and have been attracting attention since they demonstrated better effects than the conventional antiallergic drugs. On the other hand, it is also reported that leucotriene $B_4$, which is not affected by the leucotriene $C_4$ antagonist, is produced by mast cells and acidocytes and deeply involved in the allergic symptoms. Accordingly, it is considered to be most effective to inhibit the activity of 5-lipoxygenase which is a leucotriene producing enzyme, in order to control as much as possible the effect of leucotrienes which are deeply involved in the onset and evolution of the allergic symptoms.

In fact, various 5-lipoxygenase inhibitors have been proposed as a candidate compound for an antiallergic agent. However, although these candidate compounds show very strong 5-lipoxygenase inhibiting actions in vitro (the effect shown in a test tube), they scarcely show antiallergic activity in vivo (the effect shown in a living body) thus the development thereof for a medicine has been given up. This is considered to be that almost all the compounds having strong 5-lipoxygenase inhibiting actions contain a catechol skeleton as its basic skeleton and the compounds having a catechol skeleton are almost completely transformed to physiologically inactive metabolites due to the metabolism by catechol methyl transferase (COMT) in liver. In fact, the inventor had produced a chalcone derivative having a catechol skeleton for the first time as the most strong 5-lipoxygenase inhibitor (J. Med. Chem. 36, 3904(1993)), but found that when the compound was orally administered, it underwent metabolism in liver and unchanged body thereof was scarcely detected in the blood.

SUMMARY OF THE INVENTION

As a result of intensive studies, the present inventor has found that novel Compound I which does not have a catechol skeleton, has a strong anti-oxidant action (5-lipoxygenase inhibiting action) not only in vitro but also in vivo, besides, it has an antihistaminic action, and shows an excellent antiallergic action in an oral administration test on an animal, and completed the present invention. Accordingly, an object of the present invention is to provide an antiallergic agent having both leucotriene production inhibiting action and antihistaminic action, which can be orally administered.

DETAILED DESCRIPTION OF THE INVENTION

The present invention relates to an antiallergic compound having a hydroquinone skeleton represented by the following general formula

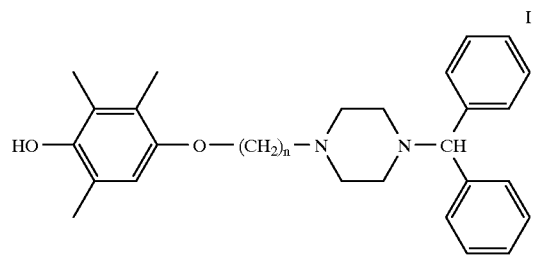

(wherein n represents an integer of 2–10), and the Compound I is found to have a leucotriene production inhibiting effect, an antihistaminic action and an oral and useful antiallergic activity.

EXAMPLES

Test Examples and Synthesis Examples will be given as Examples of the present invention.

Test Example 1 [Anti-oxidant-action (lipid peroxide production inhibiting action)]

Compounds II–VII represented by the following formulae formula

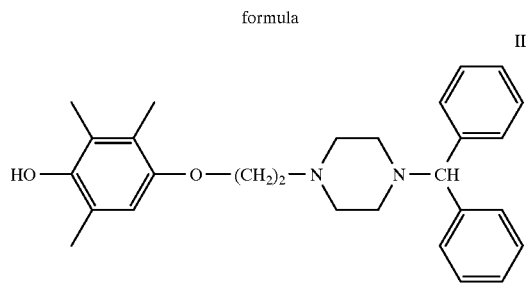

Figure 1:
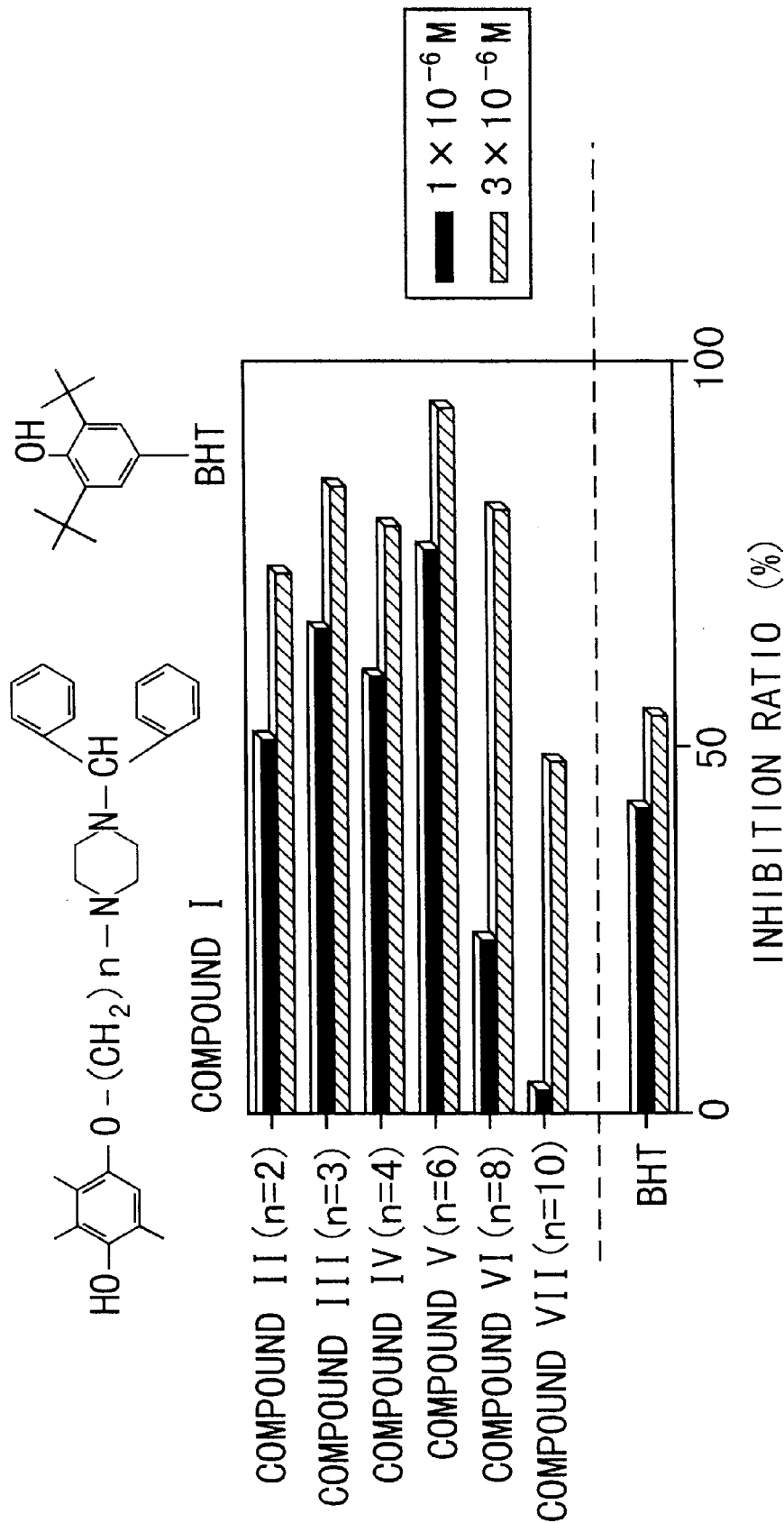
FIG. 1 is a diagram showing the effect of the Compound I and that of BHT on ADP/$Fe^{3+}$ induced lipid peroxidation reaction using rat liver microsome.

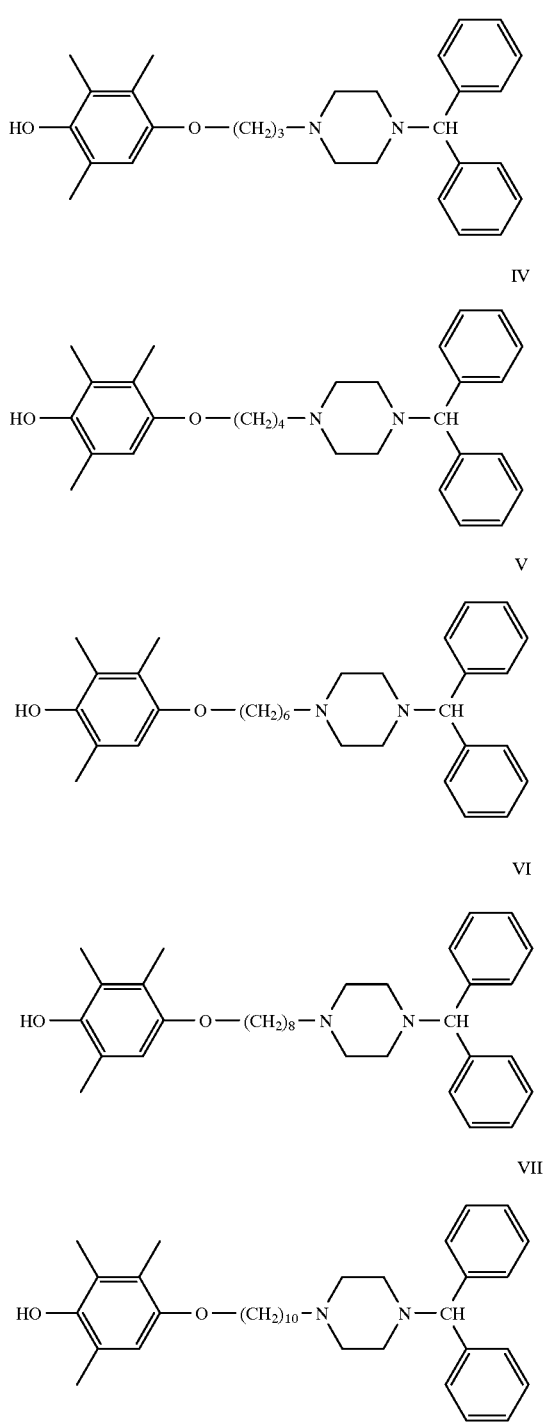

have shown concentration dependent inhibition action on ADP/$Fe^{3+}$ induced lipid peroxidation reaction using rat liver microsome. Among these, Compound II, Compound III, Compound IV, and Compound V, showed higher inhibition actions than BHT which was a positive control (FIG. 1).

Test method (ADP/$Fe^{3+}$ induced lipid peroxidation reaction)

The method of Kiso et al. was employed. That means, 100 μl of a rat liver microsome suspension (20 mg of protein/ml), 100 μl of a 2 mM NADPH, 100 μl of a 10 mM ADP, and 100 μl of a specimen solution whose concentration was controlled with a 10% N,N-dimethylformamide (DMF) aqueous solution were added to 500 μl of a trihydroxymethylaminomethane (Tris)-HCl buffer solution (167 mM KCl, 74.4 mM Tris, pH 7.4) and heated at 37° C. for 5 minutes. Then 100 μl of 100 μM $FeCl_3$ was added thereto and heated at 37° C. for 20 minutes To a control was added 100 μl of a 10% DMF aqueous solution instead of the specimen solution. To a blank, 100 μl of a 10% DMF aqueous solution was added instead of the specimen solution, and 300 μl of water was added instead of 100 μl of the NADPH, 100 μl of the $FeCl_3$, and 100 μl of the ADP. The reaction was stopped by cooling with ice, and the amount of the lipid peroxide was calculated as an amount of malondialdehyde according to the method of Ohkawa et al.

That means, 200 μl of a 8.1% sodium dodecyl sulfate (SDS) aqueous solution, 1.5 ml of an acetic acid buffer solution (20% AcOH containing 0.27M HCl was controlled with 10M NaOH to have a pH of 3.5), and 1.5 ml of a 0.8% 2-thiobarbituric acid aqueous solution were added to 1 ml of the reaction mixture and heated in a boiling water bath for 20 minutes Following heating, the reaction was stopped with cooling with ice and 4 ml of n-BuOH-pyridine mixed solution (15:1) was added thereto and mixed vigorously. Then the mixture was subjected to centrifugation at 800×g for 10 minutes and the absorbancy of the supernatant liquid was measured at 532 nm.

Test Example 2 [5-lipoxygenase inhibiting action (leucotriene production inhibiting action)]

In this test, the compound V having showed the highest anti-oxidant action in Test Example 1 was used as the specimen. The inhibition activity ($IC_{50}$) of the compound V to 5-lipoxygenase was 6.2 μM, and it was a little lower than that of a positive control compound NDGA having a catechol skeleton ($IC_{50}$=0.5 μM).

Test method (5-lipoxygenase inhibition action)

The method of Blackham et al. was employed. That means, a RBL-1 cell suspension which was adjusted with a 50 mM phosphate buffer such that the number of cells became 1×$10^7$ cells/ml, was subjected to supersonic treatment and the cells were disrupted To 500 μl of the cell homogenate solution was added 10 μl of a specimen solution whose concentration was adjusted to different concentrations using a 1% DMSO, 10 μl of 100 mM $CaCl_2$ and 10 μl of a 10 mg/ml arachidonic acid solution in MeOH and heated to 37° C. for 3 minutes. To a control was added 10 μl of a 1% DMSO instead of the specimen. To a blank, 10 μl of a 1% DMSO was added instead of the specimen, and 500 μl of a 50 mM phosphate buffer was added instead of RBL-1 cell suspension. Then 500 μl of MeOH was added thereto and the mixture was cooled with ice to stop the reaction, followed by mixing and centrifugation at 2000×g for 15 minutes Then the amount of 5-HETE in 10 μl of the supernatant liquid was measured using HPLC under the following conditions.

HPLC conditions:
column; Cosmosil $5C_{18}$ (4.6×150 mm)
mobile phase; acetonitrile: 0.1% acetic acid=85:15
flow rate; 1.0 ml/min
detection wave length; 235 nm The inhibition ratio to 5-lipoxygenase activity was calculated according to the following formula.

$$\text{Inhibition ratio } (\%) = \left(1 - \frac{\text{specimen} - \text{blank}}{\text{control} - \text{blank}}\right) \times 100$$

area; peak area

Test Example 3—Antihistaminic action

In this test, the compound V having showed the highest anti-oxidant action in the Test Example 1 was used as the specimen. The antihistaminic action of the Compound V was tested with a guinea pig bowel by Magnus' method using diphenhydramine hydrochloride as a positive control. As a result, $pA_2$ which represents an index of the antihistaminic action of the Compound V was 6.90.

Method (Magnus' method)

A guinea pig which had been fasted overnight was struck to death and the ileum was excised to a length of about 2 cm and one end was suspended in an isotonic transducer and the other end was secured onto a fixed rod. The temperature of the temperature controlled bath was kept at 37° C. and the ileum was allowed to stand for about 30 minutes while a mixed gas comprising 95% of $O_2$ and 5% of $CO_2$ was introduced into 10 ml of Tyrode solution, and histamine of different concentrations was injected for training, then a dose reaction curve was obtained by administering histamine accumulatively in order of increasing concentration. Then after washing, a dose reaction curve in relation to the histamine was similarly obtained under administration of the specimen and $pA_2$ was calculated.

Test Example 4—Antiallergic action in an orally administered rat (PCA method)

The antiallergic actions of Compound II–Compound VII were evaluated using rat cutaneous anaphylactic reaction (PCA reaction) employing tranilast, which is an oral antiallergic agent, as a positive control compound. As a result, Compound III–Compound VI showed antiallergic activity even through oral administration and in particular, Compound IV and Compound V showed higher activity than that of the positive control compound.

Test method (Antiallergic action by PCA reaction)

Figure 2:
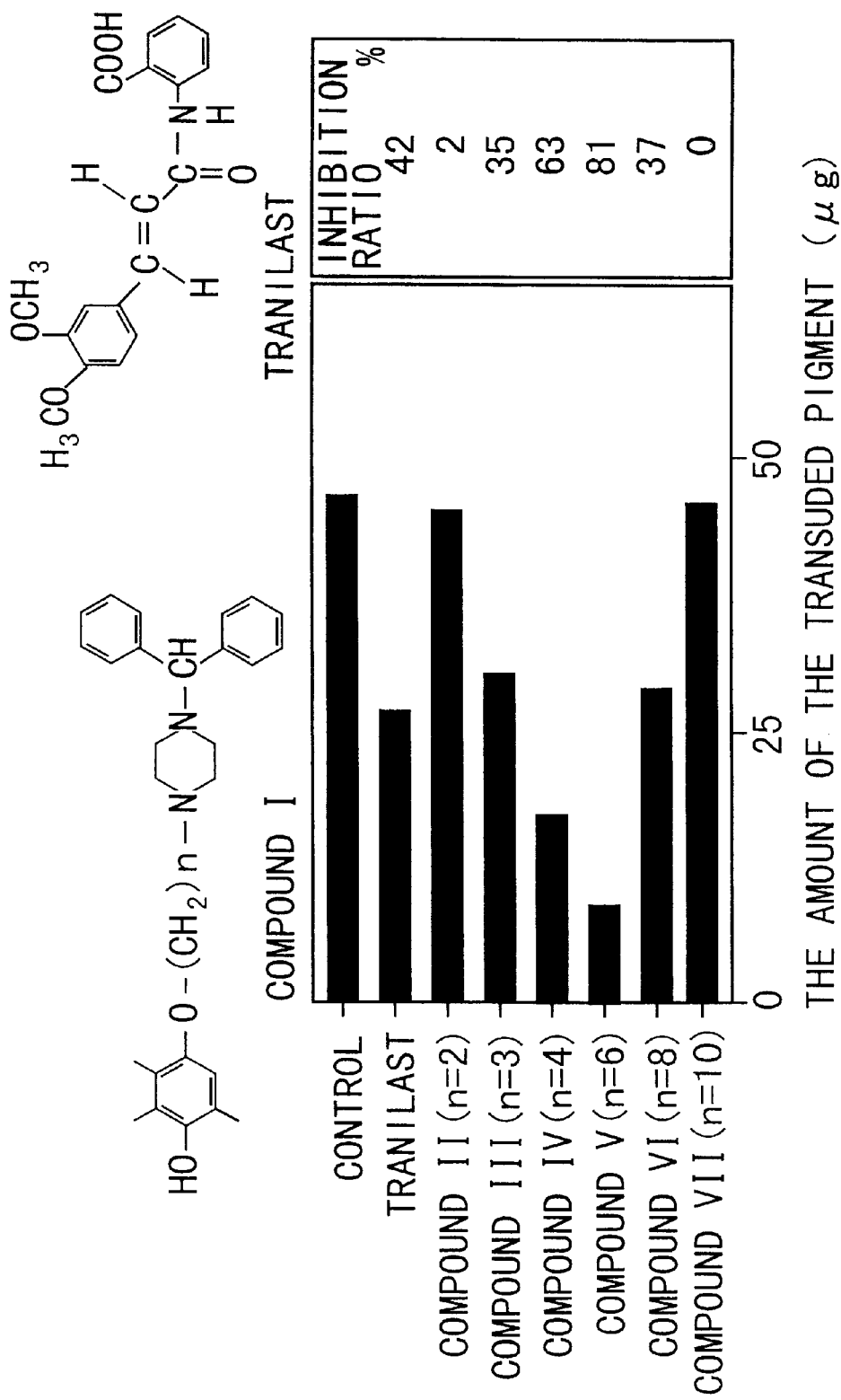
FIG. 2 is a diagram showing the effect of the Compound I and that of tranilast on 48 hours homologous PCA reaction on a rat's back skin.

The test was carried out according to the method of Koda et al, {Int. Arch. Allergy Appl. Immunol. 87, 254(1988)}. The dorsum of a Wistar-strain male rat having a body weight of about 200 g was shaved and 0.1 ml of an antiserum showing 48 hours homologous PCA strength of 1:128–1:256 diluted with physiological saline was injected into the dorsum intracutaneously. After 48 hours, 1 ml of 0.5% Evans blue physiological saline containing DNP-BSA in an amount of 1 mg in terms of protein, was injected into the caudal vein. After 30 minutes, the rat was brought to death by exsanguination and the pigment freckle generated on the back skin was cut out and the amount of the transuded pigment was determined. That means, the cut out skin was put in a test tube, 1 ml of 1N KOH was added and allowed to stand overnight at 37° C. to elute the pigment, and 9 ml of a mixture comprising acetone and 0.6N phosphoric acid (mixed at 13:5) was added thereto and shaken, and the insoluble substances were removed by filtration and the absorbency of the filtrate was measured at 620 nm and the amount of the pigment was determined. The specimen was suspended in 0.2% CMC-Na, and controlled such that the specimen was given to the rat in an amount of 0.5 ml per 100 g of the rat body weight, and orally administered 2 hours before the administration of the antigen. The results are shown in FIG. 2.

Synthetic Example 1

Synthesis method of hydroquinone derivative Compound II

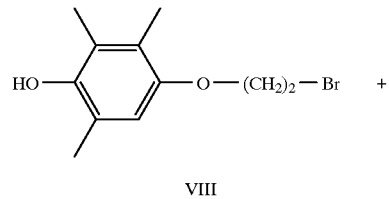

VIII

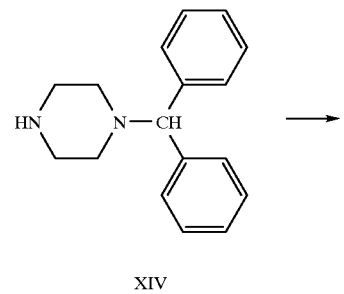

XIV

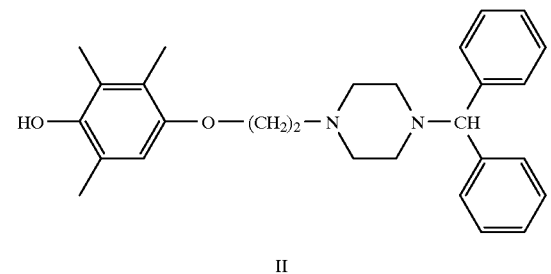

II (1) Trimethylhydroquinone (10.0 g, 66 mmol) and 2-bromo-1-ethanol (8.4 g, 66 mmol) were dissolved in toluene (40 ml) and phosphomolybdic acid (1.92 g) was added thereto and subjected to reflux for 24 hours. Then it was filtered by aspiration using Celite and the solvent was removed by rotary evaporator under a reduced pressure and purification was carried out using silica gel column chromatograph (hexane:benzene=1:5) to give white Compound VIII (8.0 g, 47%, mp 105°–107° C.).

(2) Compound VIII (1 g, 3.86 mmol) and Compound XIV (0.974 g, 3.86 mmol) were dissolved in acetonitrile (20 ml) and potassium carbonate (1.08 g, 7.72 mmol) was added thereto and subjected to reflux for 20 hours. Then it was filtered by aspiration and the solvent was removed by rotary evaporator under a reduced pressure then purified by silica gel column chromatograph (hexane:ethyl acetate=2:1) to give white Compound II (0.6 g, 36%, mp 147°–149° C.).

Compound II $^1$HNMR (200 MHz, $CDCl_3$)δ2.09(s, 3H) 2.12(s, 3H) 2.15(s, 3H) 2.44(bs, 4H) 2.63(bs, 4H).2.79(t, J=5.7 Hz, 2H) 3.95(t, J=5.7 Hz, 2H) 4.18(s, 1H) 6.43(s, 1H) 7.14–7.42(m, 10H); MS (EI-DI) 430($M^+$)

Hydrochloride mp 142°–145° C.

Synthetic Example 2

Synthesis method of hydroquinone derivative Compound III

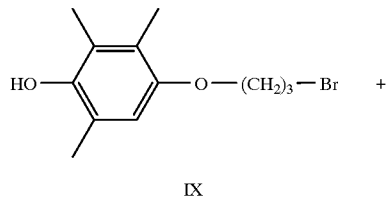

IX

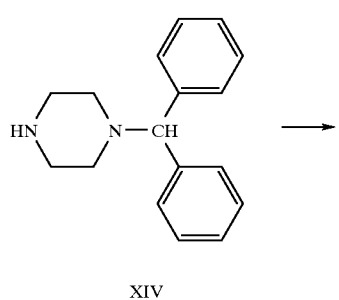

XIV

↓

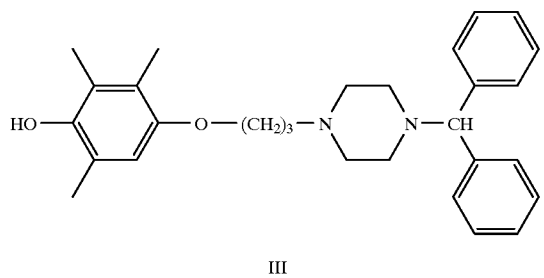

III

Hydrochloride mp 211°–213° C.

Synthesis Example 3

Synthesis method of hydroquinone derivative Compound IV

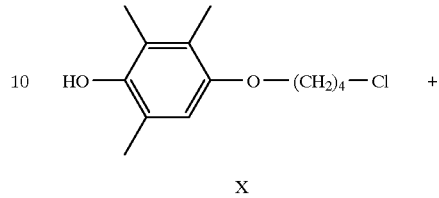

X

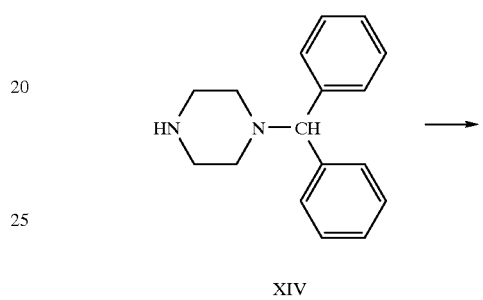

XIV

↓

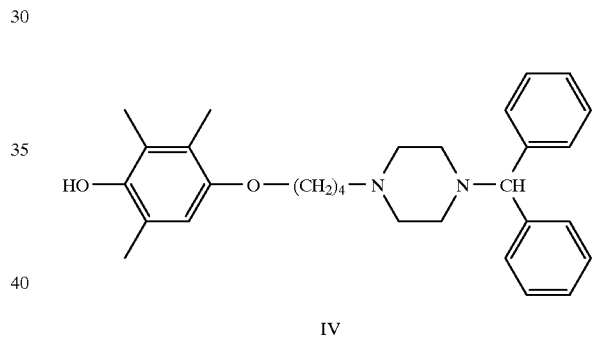

IV (1) Trimethylhydroquinone (7.6 g, 50 mmol) and 3-bromo-1-propanol (7.0 g, 50 ol) were dissolved in toluene (40 ml) and phosphomolybdic acid (1.0 g) was added and subjected to reflux for 24 hours. It was filtered by aspiration using Celite and the solvent was removed by rotary evaporator under a reduced pressure then purification was carried out using silica gel column chromatograph (hexane:ethyl acetate=7:1) to give white Compound IX (5.4 g, 40%, mp 60°–62° C.).

(2) Compound IX (1 g, 3.66 mmol) and Compound XIV (0.924 g, 3.66 mmol) were dissolved in acetonitrile (20 ml) and potassium carbonate (1.01 g, 7.32 mmol) was added thereto and subjected to reflux for 20 hours. Then it was filtered by aspiration and the solvent was removed by rotary evaporator under a reduced pressure then purification was carried out using silica gel column chromatograph (hexane:ethyl acetate=2:1) to give white Compound III (0.776 g, 48%, mp 47.5°–50° C.).

Compound III $^1$HNMR (200 MHz, CDCl$_3$)δ1.92(tt, J=6.1 Hz, 2H) 2.11(s, 3H) 2.13(s, 3H) 2.17(s, 3H) 2.44(bs, 4H) 2.49(t, J=6.1 Hz, 2H) 2.53(bs, 4H) 3.84(t, J=6.1Hz, 2H) 4.18(s, 1H) 6.47(s, 1H) 7.10–7.42(m, 10H); MS(EI-DI) 444(M$^+$)

(1) Trimethylhydroquinone (2.0 g, 13.1 mmol) and 4-chloro-1-butanol (1.4 g, 13.1 mmol) were dissolved in toluene (20 ml) and phosphomolybdic acid (0.5 g) was added and subjected to reflux for 24 hours. It was filtered by aspiration using Celite and the solvent was removed by rotary evaporator under a reduced pressure then purification was carried out using silica gel column chromatograph (hexane:ethyl acetate=10:1) to give white Compound X (1.4 g, 44%, mp 58°–59° C.)

2) Compound X (1.0 g, 4.12 mmol) and compound XIV (1.04 g, 4.12 mmol) were dissolved in acetonitrile (20 ml) and potassium carbonate (1.14 g, 8.24 mmol) was added thereto and subjected to reflux for 24 hours. Then it was filtered by aspiration and the solvent was removed by rotary evaporator under a reduced pressure then purification was carried out using silica gel column chromatograph (hexane:ethyl acetate=2:1) to give white Compound IV (1.4 g, 74%, mp 46°–48° C.).

Compound IV
$^1$HNMR (200 MHz, CDCl$_3$)δ1.63–1.78(m, 4H) 2.12(s, 3H) 2.16(s, 3H) 2.21(s, 3H) 2.36–2.51(m, 10H) 3.87(t, J=6.1 Hz, 2H) 4.21(s, 1H) 6.49(s, 1H) 7.16–7.44(m, 10H); MS(EI-DI) 458(M$^+$)

Hydrochloride mp 141°–143°C.

Synthesis Example 4

Synthesis method of hydroquinone derivative
Compound V

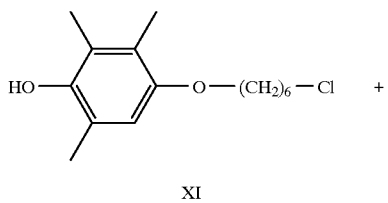

XI

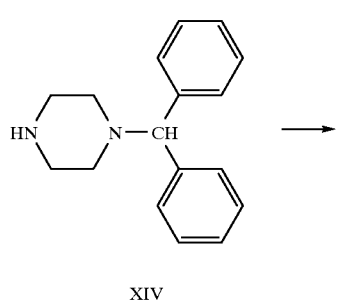

XIV

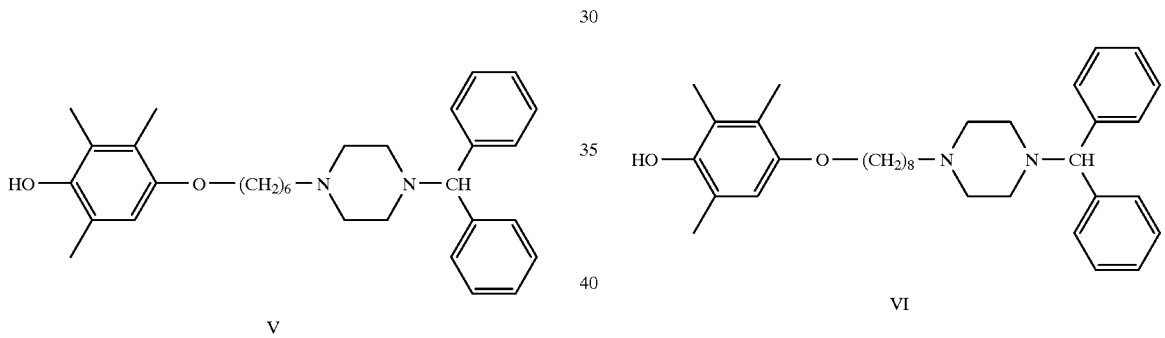

V

Synthesis Example 5

Synthesis method of hydroquinone derivative
Compound VI

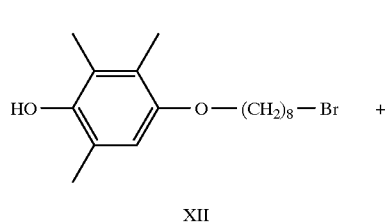

XII

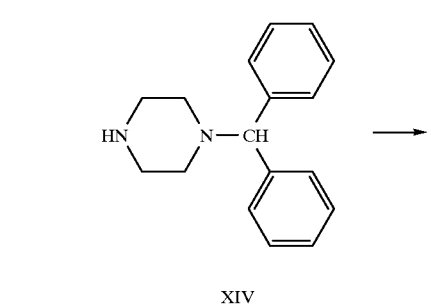

XIV

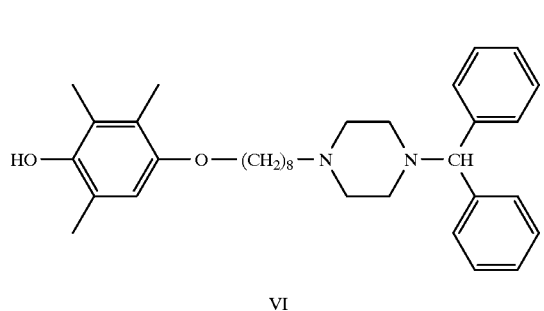

VI (1) Trimethylhydroquinone (1.0 g, 6.6 mmol) and 6-chloro-1-hexanol (0.9 g, 6.6 mmol) were dissolved in toluene (20 ml) and phosphomolybdic acid (0.5 g) was added and subjected to reflux for 24hours. It was filtered by aspiration using Celite and the solvent was removed by rotary evaporator under a reduced pressure then purification was carried out-using silica gel column chromatograph (hexane:ethyl acetate=14:1) to give white Compound XI (1.02 g, 57%, mp 44°–46° C.).

(2) Compound XI (1 g, 3.69 mmol) and compound XIV (0.932 g, 3.69 mmol) were dissolved in acetonitrile (20 ml) and potassium carbonate (1.01 g, 7.38 mmol) was added thereto and subjected to reflux for 20 hours. Then it was filtered by aspiration and the solvent was removed by rotary evaporator under a reduced pressure then purified by silica gel column chromatograph (hexane:ethyl acetate=2:1) to give white Compound V (0.9 g, 50%, mp42°–43° C.).

Compound V
$^1$HNMR (200 MHz, CDCl$_3$)δ1.26–1.82(m, 8H) 2.13(s, 3H) 2.16(s, 3H) 2.21(s, 3H) 2.33(t, J=7.3 Hz, 2H) 2.45(m, 8H) 3.85(t, J=6.6 Hz, 2H) 4.20(s, 1H) 6.50(s, 1H) 7.15–7.42 (m, 10H); MS(EI-DI) 486(M$^+$)

Hydrochloride mp 155°–157° C.

(1) Trimethylhydroquinone (0.8 g 5.26 mmol) and 8-bromo-1-octanol (1.1 g, 5.26 mmol) were dissolved in toluene (20 ml) and phosphomolybdic acid (0.5 g) was added and subjected to reflux for 24 hours. It was filtered by aspiration using Celite and the solvent was removed by rotary evaporator under a reduced pressure then purification was carried out using silica gel column chromatograph (hexane:ethyl acetate=8:1) to give white Compound XII (1.03 g, 57%, mp 62°–64° C.).

(2) Compound XII (2 g, 5.82 mmol) and compound 1.47 g, 5.82 mmol) were dissolved in. acetonitrile (20 ml) and potassium carbonate (1.61 g, 11.64 mmol) was added thereto and subjected to reflux for 20 hours. Then it was filtered by aspiration and the solvent was removed by rotary evaporator under a reduced pressure then purification was carried out using silica gel column chromatograph (hexane:ethyl acetate=2:1) to give white Compound VI (2.00 g 67%, oil).

Compound VI $^1$HNMR (200 MHz, CDCl$_3$)δ1.2–1.79(m, 12H) 2.13(s, 3H) 2.17(s, 3H) 2.21(s, 3H) 2.26–2.53(m, 10H) 3.85(t, J=6.5 Hz, 2H) 4.21(s, 1H) 6.51(s, 1H) 7.16–7.43(m, 10 H); MS(EI-DI) 514(M$^+$)

Hydrochloride mp 179°–182° C.

Synthesis Example 6

Synthesis method of hydroquinone derivative Compound VII

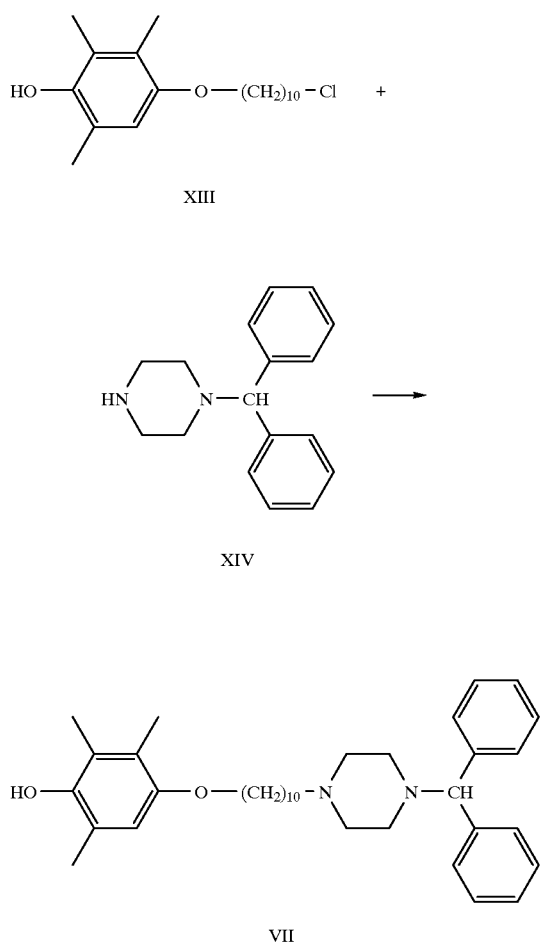

(1) Trimethylhydroquinone (4.0 g, 26.3 mmol) and 10-chloro-1-decanol (5.06 g, 26.3 mmol) were dissolved in toluene (30 ml) and phosphomolybdic acid (1.0 g) was added and subjected to reflux for 24 hours. It was filtered by aspiration using Celite and the solvent was removed by rotary evaporator under a reduced pressure then purification was carried out using silica gel column chromatograph (hexane:ethyl acetate=20:1) to give white Compound XIII (6.0 g, 70%, mp 57°–58° C.).

(2) Compound XIII (3 g, 9.18 mmol) and Compound XIV (2.32 g, 9.18 mmol) were dissolved in acetonitrile (20 ml) and potassium carbonate (2.54 g, 18.36 mmol) was added thereto and subjected to reflux for 20 hours. Then it was filtered by aspiration and the solvent was removed by rotary evaporator under a reduced pressure then purification was carried out using silica gel column chromatograph (hexane:ethyl acetate=2:1) to give white Compound VII (3.0 g, 60%, oil).

Compound VII $^1$HNMR (200 MHz, CDCl$_3$)δ1.21–1.78(m, 16H) 2.13(s, 3H) 2.15(s, 3H) 2.20(s, 3H) 2.29(t, J=6.5 Hz, 2H) 2.34–2.44 (m, 8H) 3.86(t, J=6.5 Hz, 2H) 4.19(s, 1H) 6.50(s, 1H) 6.50(s, 1H) 7.15–7.43(m, 10H); MS(EI-DI) 542(M$^+$)

Hydrochloride salt mp 182°–185° C.

What is claimed is:

1. A hydroquinone derivative represented by the following formula:

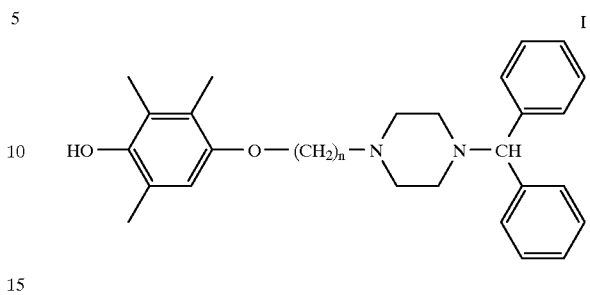

wherein is an integer between 2 and 10 inclusive or a hydrochloride salt of the derivative.

2. A hydroquinone derivative according to claim 1 represented by the following formula:

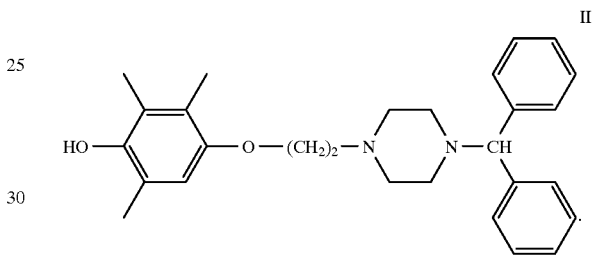

3. A hydroquinone derivative according to claim 1 represented by the following formula:

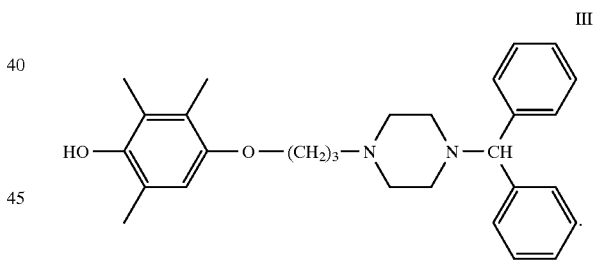

4. A hydroquinone derivative according to claim 1 represented by the following formula:

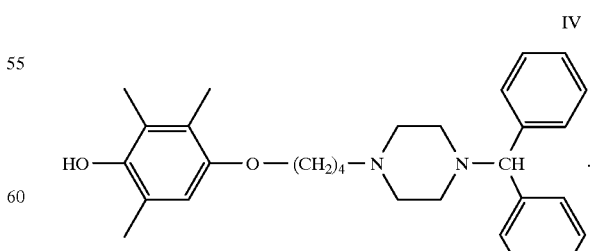

5. A hydroquinone derivative according to claim 1 represented by the following formula:

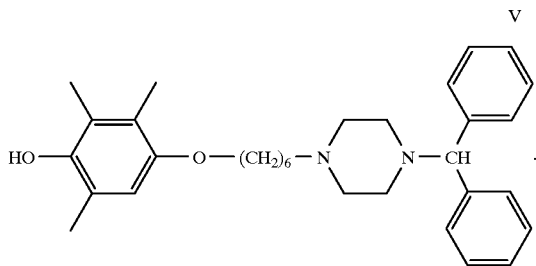

6. A hydroquinone derivative according to claim 1 represented by the following formula:

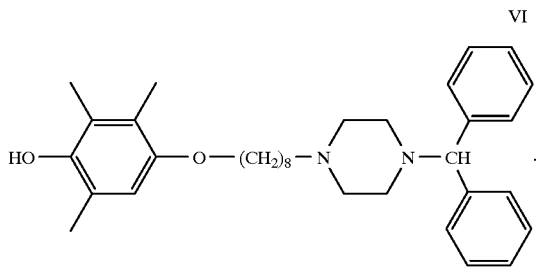

7. A hydroquinone derivative according to claim 1 represented by the following formula:

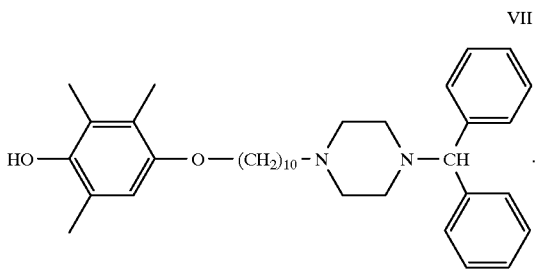

8. A hydrochloride salt of the hydroquinone derivative as described in claim 1.

9. A hydrochloride salt of the hydroquinone derivative as described in claim 2.

10. A hydrochloride salt of the hydroquinone derivative as described in claim 3.

11. A hydrochloride salt of the hydroquinone derivative as described in claim 4.

12. A hydrochloride salt of the hydroquinone derivative as described in claim 5.

13. A hydrochloride salt of the hydroquinone derivative as described in claim 6.

14. A hydrochloride salt of the hydroquinone derivative as described in claim 7.

15. A method of treating allergies in mammals comprising administering a composition comprising a hydroquinone derivative represented by the following formula:

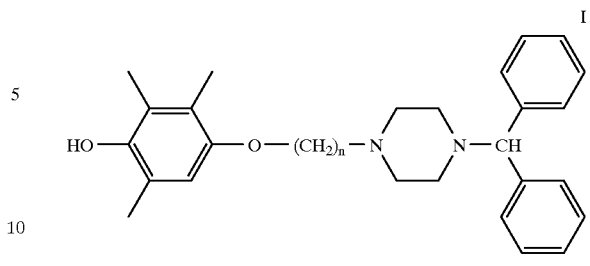

wherein n is an integer between 2 and 10 inclusive, or a hydrochloride salt of the derivative.

16. The method of claim 15 in which said administered composition comprises a hydroquinone derivative represented by the following formula:

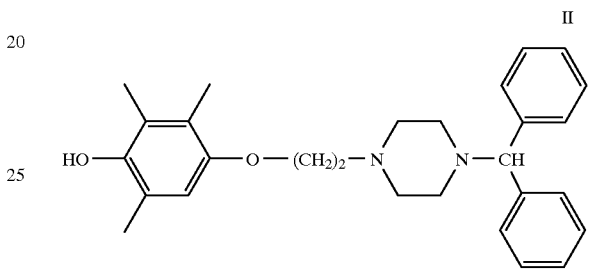

or a hydrochloride salt of the derivative.

17. The method of claim 15 in which said administered composition comprises a hydroquinone derivative represented by the following formula:

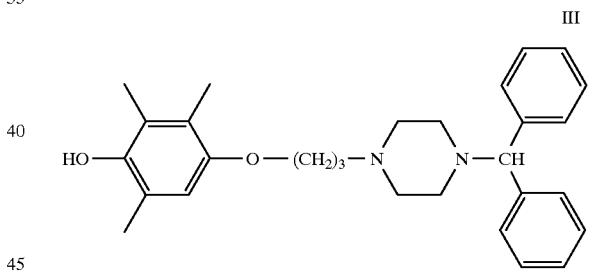

or a hydrochloride salt of the derivative.

18. The method of claim 15 in which said administered composition comprises a hydroquinone derivative represented by the following formula:

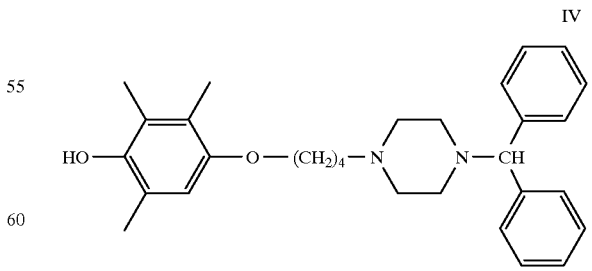

or a hydrochloride salt of the derivative.

19. The method of claim 15 in which said administered composition comprises a hydroquinone derivative represented by the following formula:

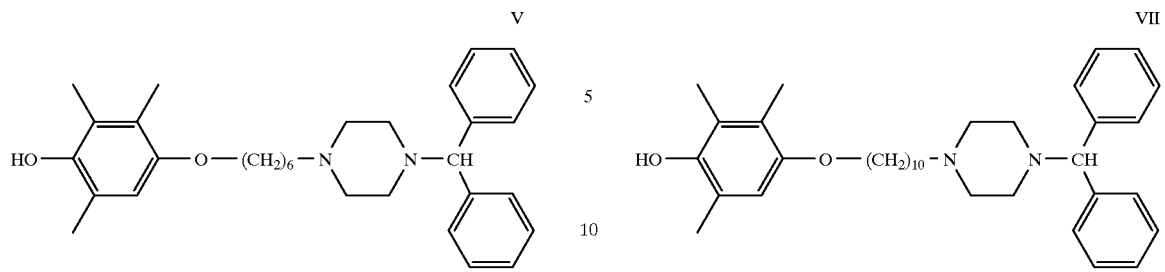

or a hydrochloride salt of the derivative.

20. The method of claim 15 in which said administered composition comprises a hydroquinone derivative represented by the following formula:

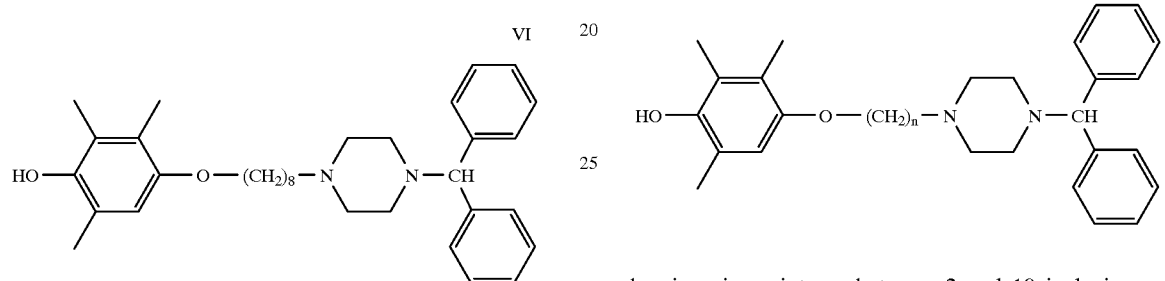

or a hydrochloride salt of the derivative.

21. The method of claim 15 in which said administered composition comprises a hydroquinone derivative represented by the following formula:

or a hydrochloride salt of the derivative.

22. A pharmaceutical composition comprising a hydroquinone derivative represented by the following formula:

wherein n is an integer between 2 and 10 inclusive, or a hydrochloride salt of the derivative, combined with a suitable pharmaceutical carrier or diluent.

23. A pharmaceutical composition of claim 22 in which said hydroquinone derivative is used in the form of its hydrochloride salt.

* * * * *

UNITED STATES PATENT AND TRADEMARK OFFICE
CERTIFICATE OF CORRECTION

PATENT NO.   : 5,910,499
DATED        : June 8, 1999
INVENTOR(S)  : Satoh et al.

It is certified that error appears in the above-identified patent and that said Letters Patent is hereby corrected as shown below:

Column 4, line 23;

After "20 minutes" insert - - . (period) - -.

Column 12, claim 1, line 18;

"wherein is" should be - - wherein n is - -.

Signed and Sealed this

Twenty-fifth Day of January, 2000

Attest:

Attesting Officer

*Acting Commissioner of Patents and Trademarks*